United States Patent
Keller

(10) Patent No.: US 6,428,563 B1
(45) Date of Patent: Aug. 6, 2002

(54) HEAT EXCHANGE CATHETER WITH IMPROVED INSULATED REGION

(75) Inventor: Wade A. Keller, San Jose, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 09/489,142

(22) Filed: Jan. 21, 2000

(51) Int. Cl.[7] .................................................. A61F 7/00
(52) U.S. Cl. .......................... 607/105; 607/106; 606/20; 606/23
(58) Field of Search ................................. 607/104, 105, 607/106, 107, 113; 606/96, 27–31, 20, 21

(56) References Cited

U.S. PATENT DOCUMENTS

| 5,151,100 | A |   | 9/1992 | Abele etr al. |
|---|---|---|---|---|
| 5,222,938 | A |   | 6/1993 | Behl |
| 5,486,208 | A | * | 1/1996 | Ginsburg ............... 607/106 |
| 5,624,392 | A |   | 4/1997 | Saab |
| 5,928,181 | A | * | 7/1999 | Coleman et al. ............ 604/8 |
| 5,957,963 | A | * | 9/1999 | Dobak ..................... 607/104 |
| 6,042,559 | A | * | 3/2000 | Dobak ......................... 604/7 |
| 6,051,019 | A | * | 4/2000 | Dobak ..................... 607/104 |

FOREIGN PATENT DOCUMENTS

EP        0 801 938 A2    10/1997
WO       WO 99/66970      12/1999

* cited by examiner

Primary Examiner—Michael Peffley
Assistant Examiner—Pete Vrettakos
(74) Attorney, Agent, or Firm—Robert D. Buyan; Stout, Uxa, Buyan & Mullins, LLP

(57) ABSTRACT

A heat exchange catheter having an expandable insulating region thereon. The catheter has a heat exchange region and the insulating region disposed proximally thereto. The insulating region assumes a first size about a catheter shaft to facilitate insertion of the catheter into the body. Once the insulating region is inserted into the body, the insulating region is expanded a second size. The insulating region may be a balloon around the catheter shaft that is inflated to the second size to create a gap between the wall of the balloon and the catheter shaft. Heat flows through the catheter shaft to and from the heat exchange region, and thus heat loss or gain to and from the surrounding body is minimized in the insulating region. The exchange region may include a fluid circulation path comprised of lumens through the catheter shaft. A particularly useful application of the catheter is for regional cooling of blood flowing to a particular location, for example to the brain, or blood flowing to the heart to treat heart attack victims. The expandable insulating region is easy to insert through an incision or introducer sheath and expands to provide an efficient thermal barrier between the fluid circulating in the shaft and a surrounding body fluid or tissue.

31 Claims, 13 Drawing Sheets

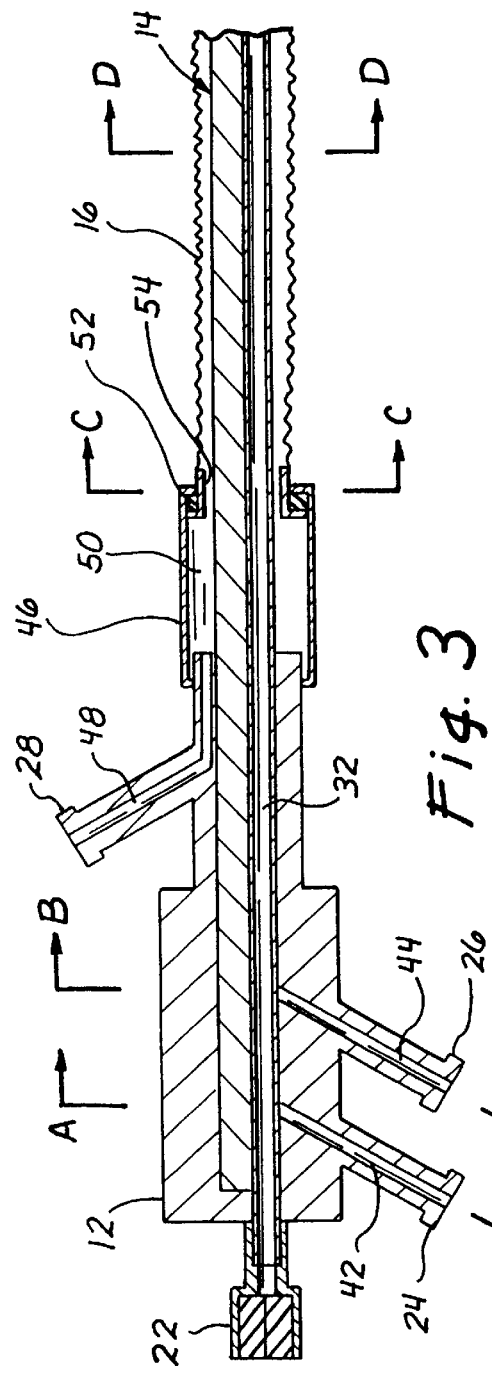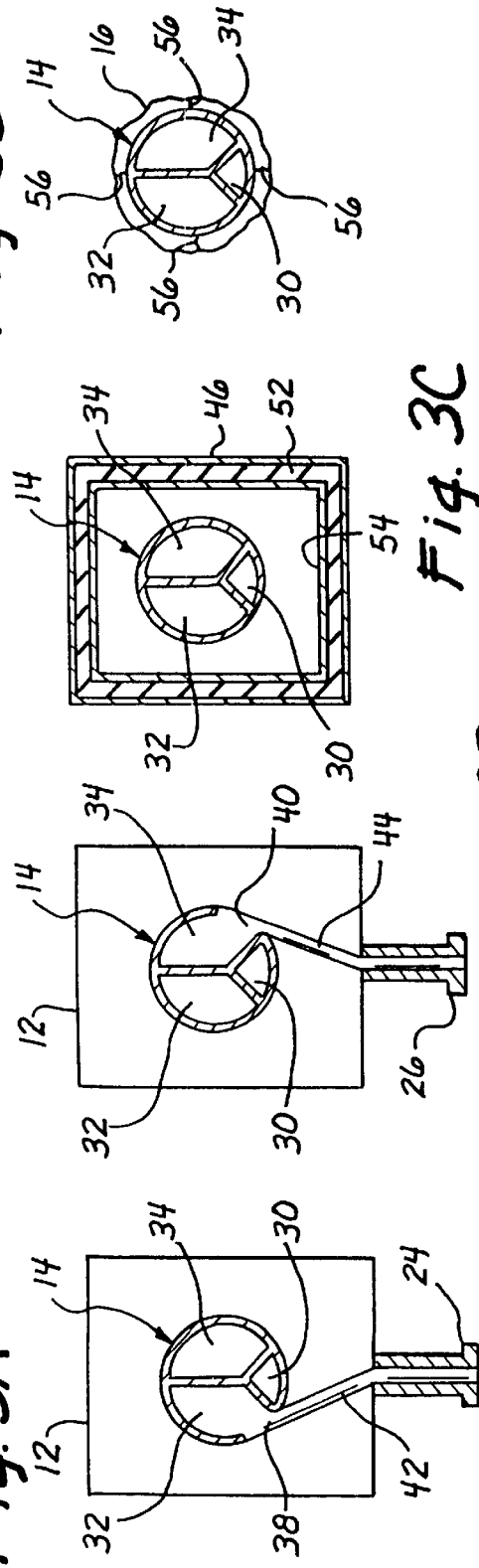
Fig. 3
Fig. 3A
Fig. 3B
Fig. 3C
Fig. 3D

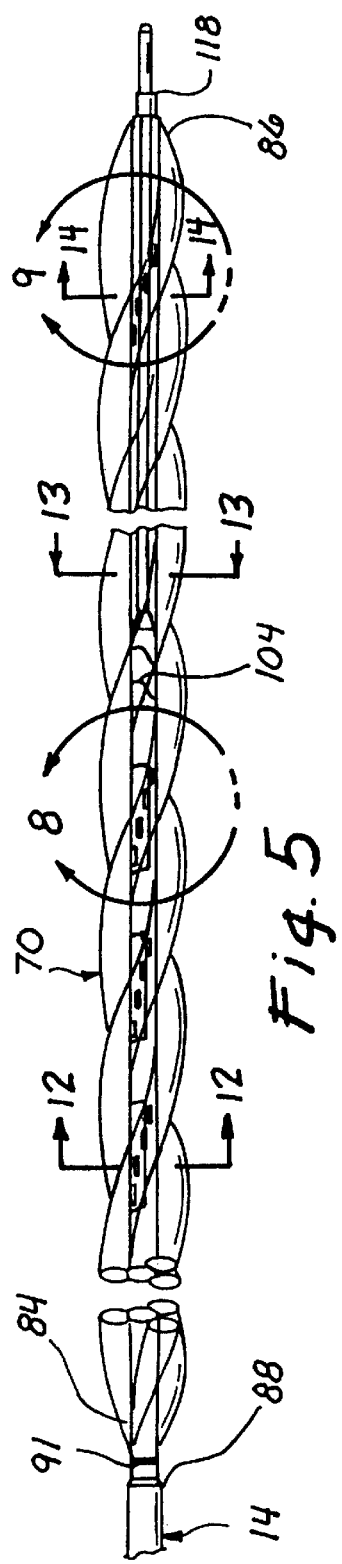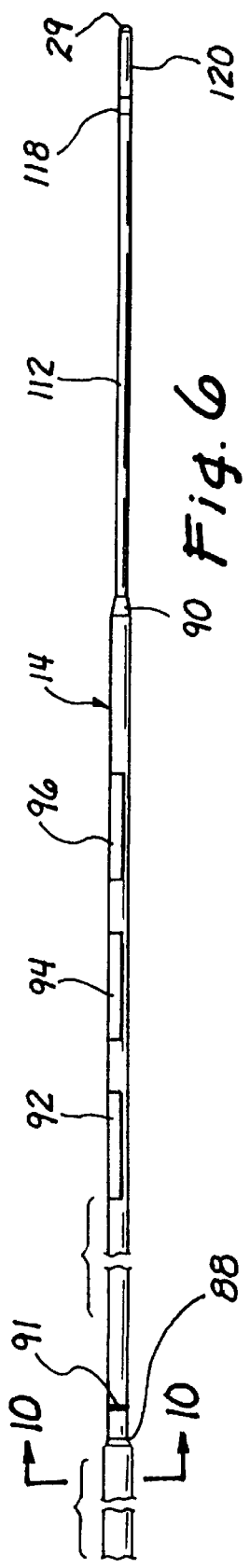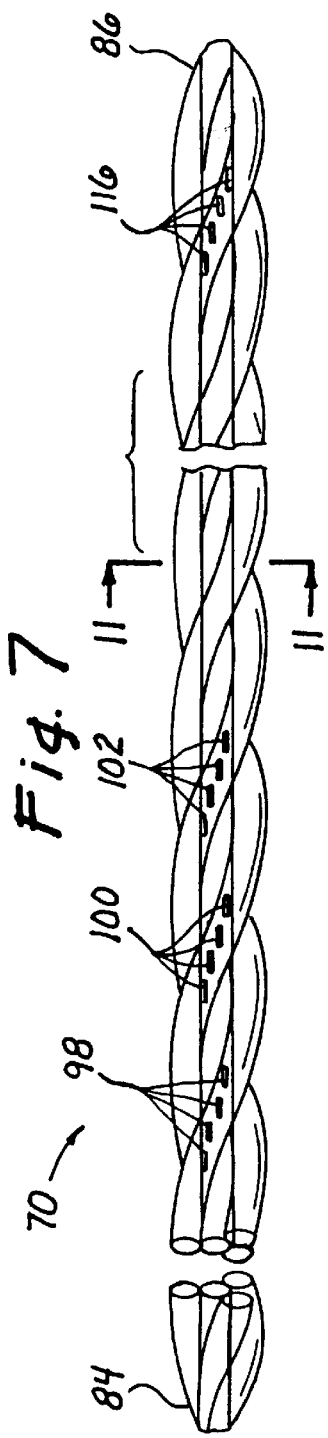

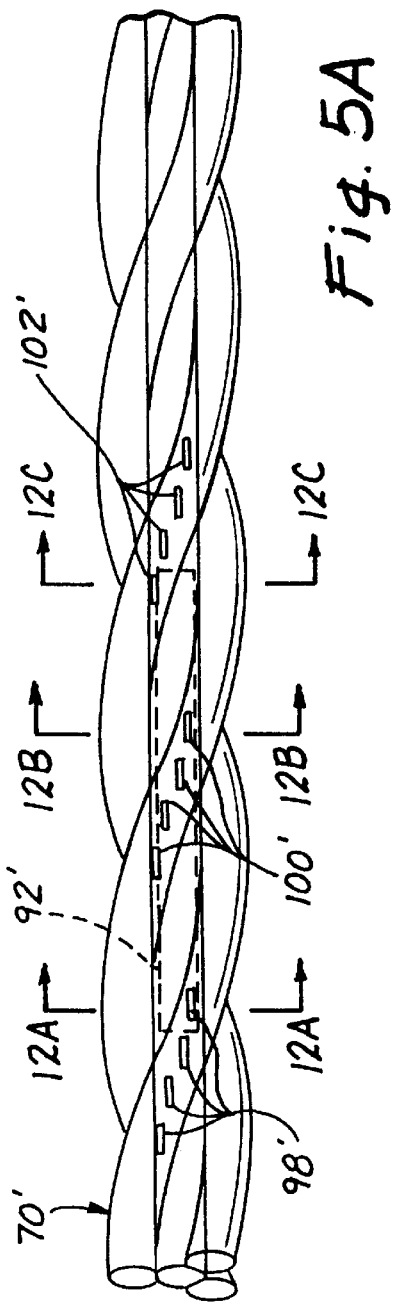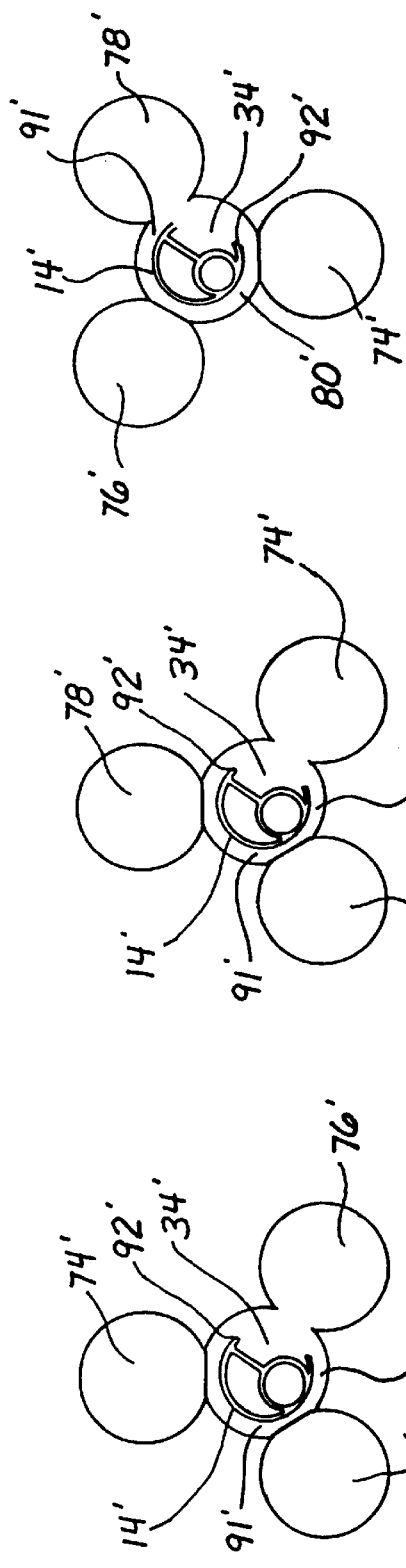

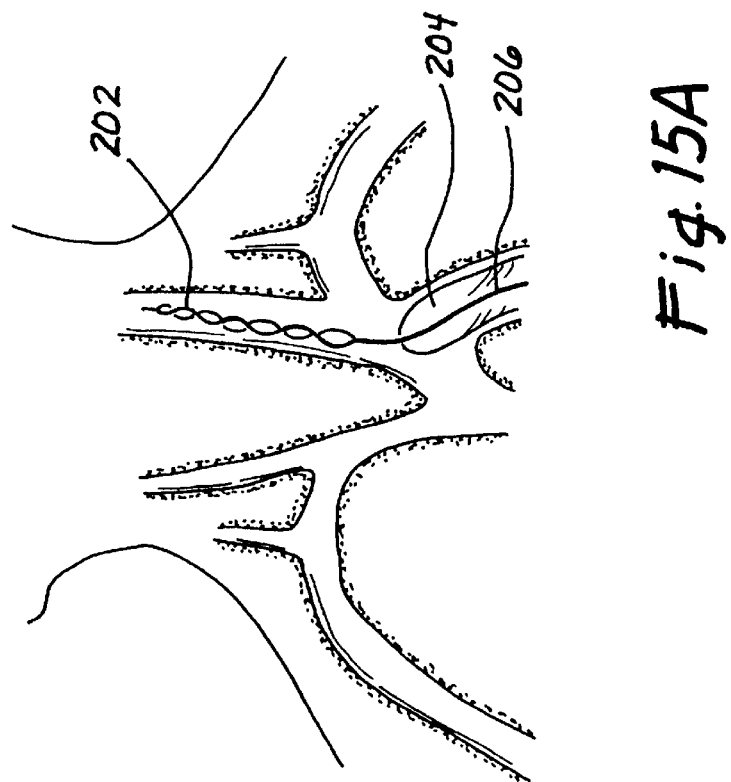
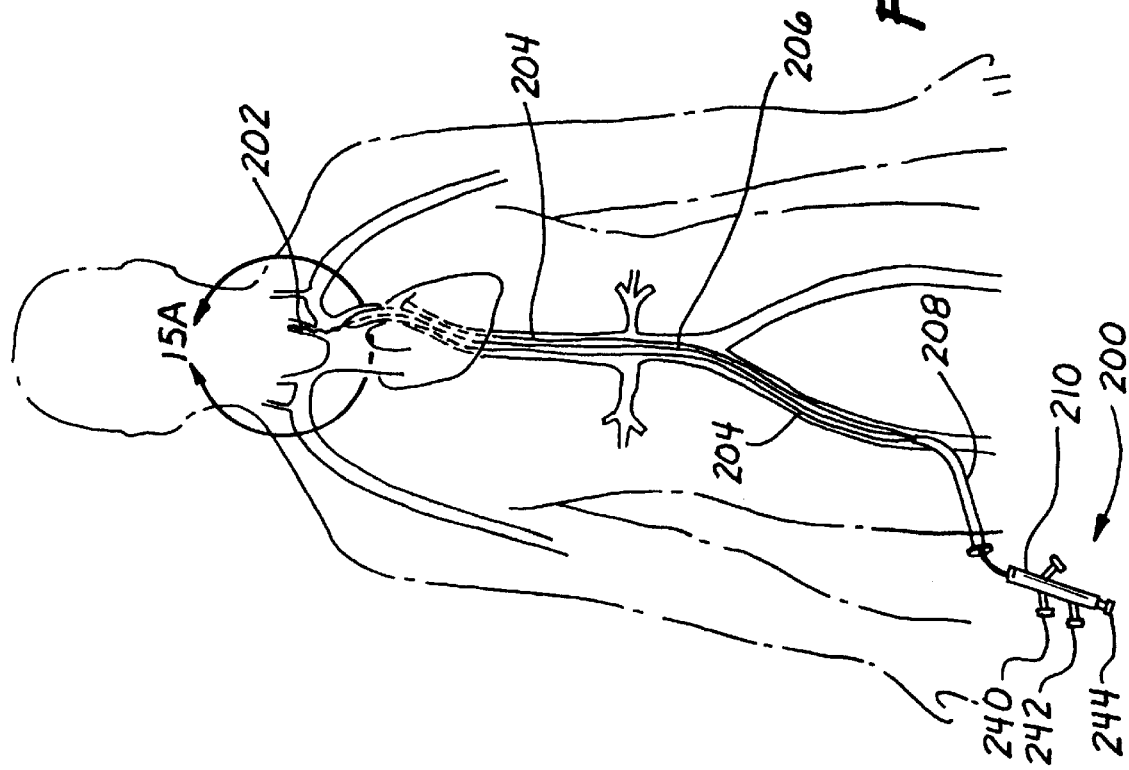
Fig. 15A
Fig. 15

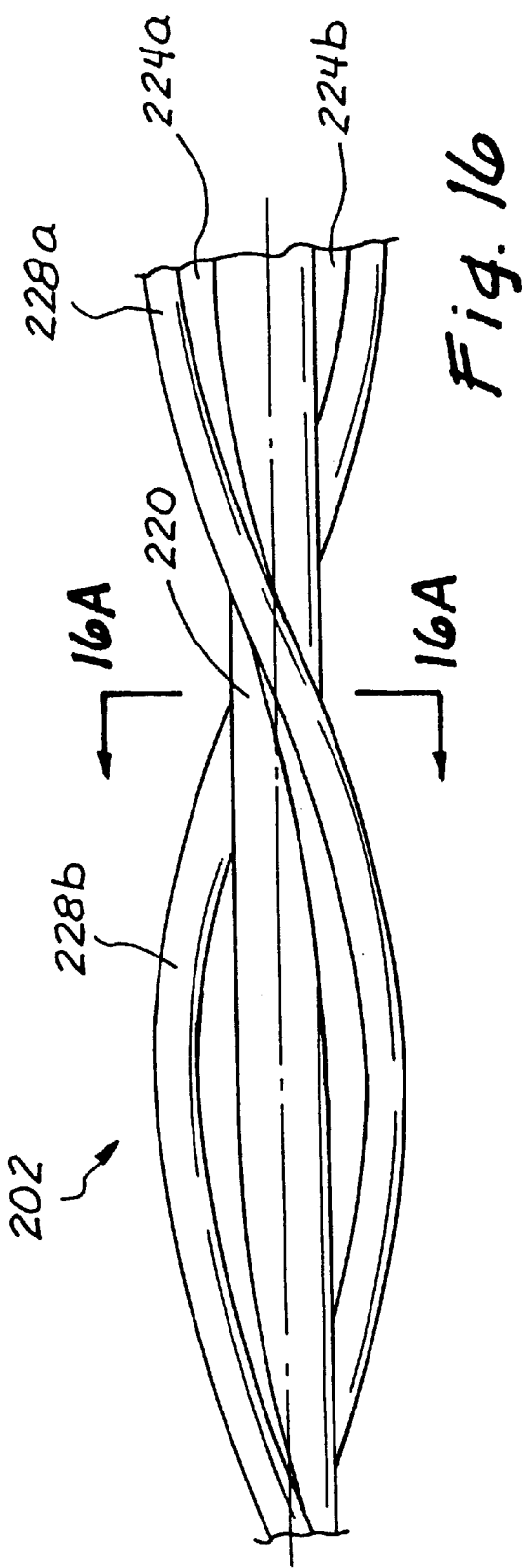
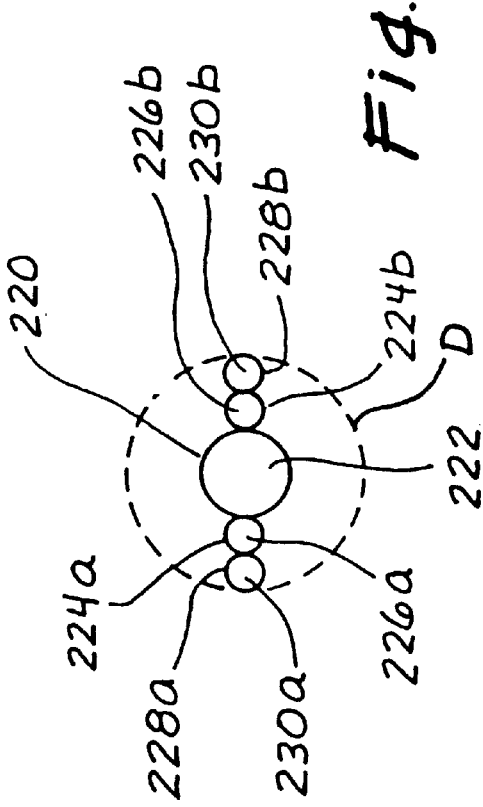

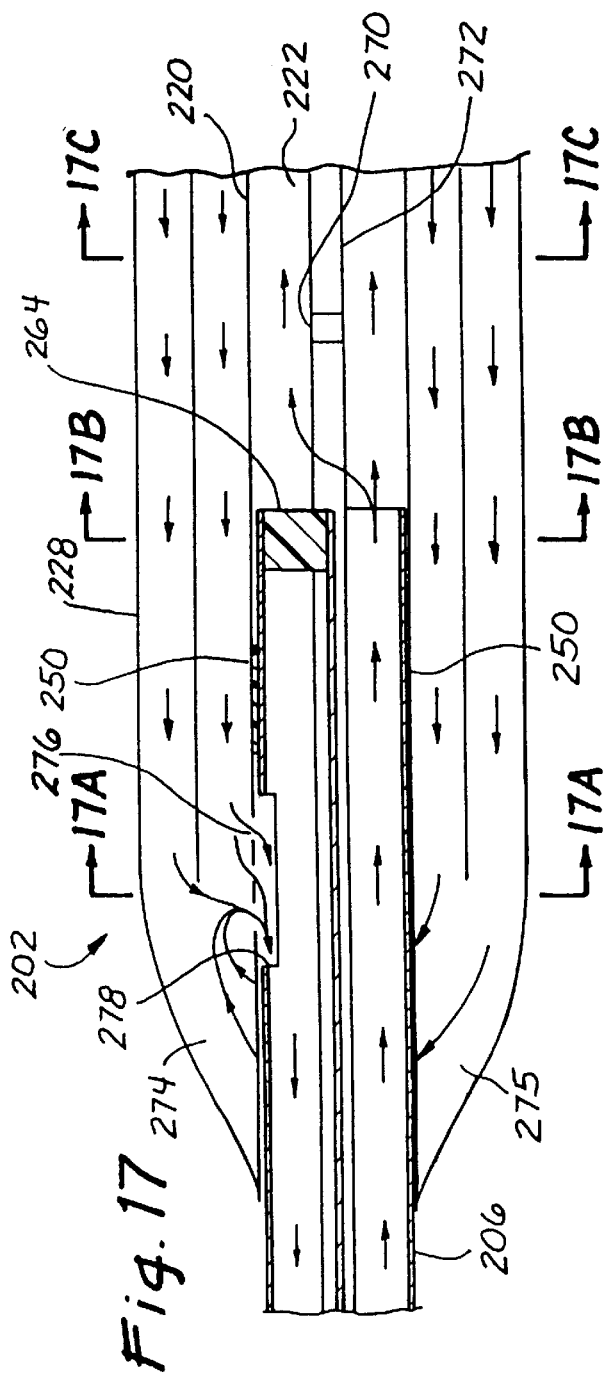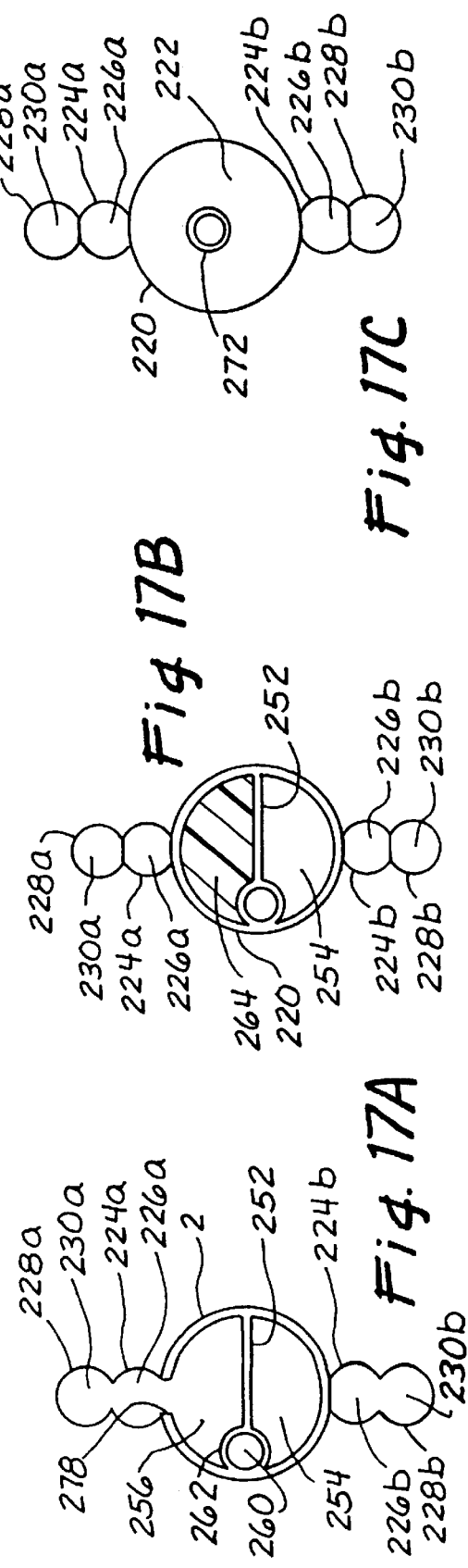

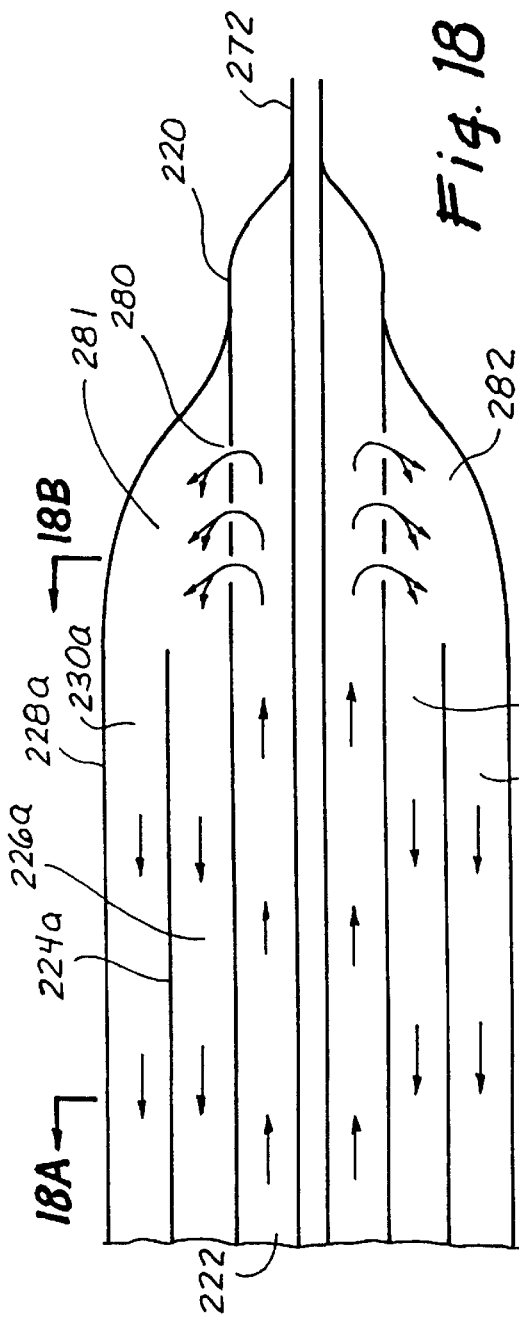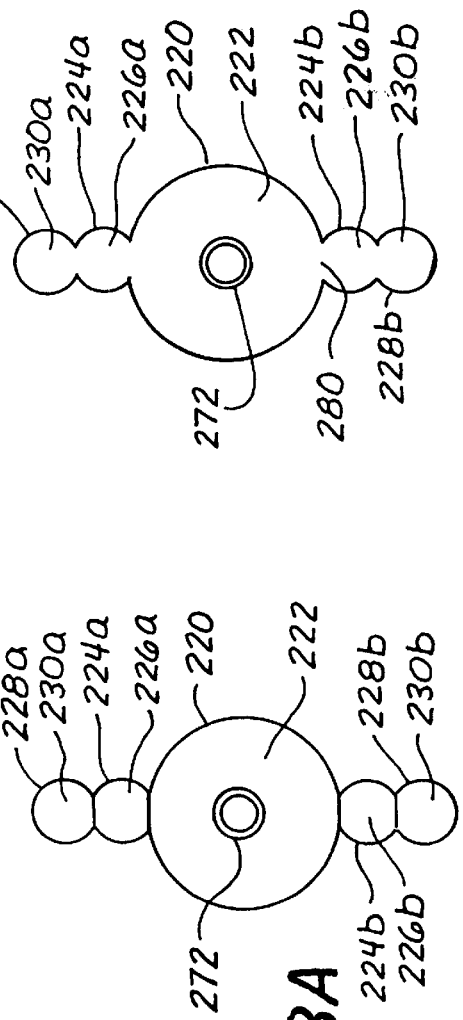

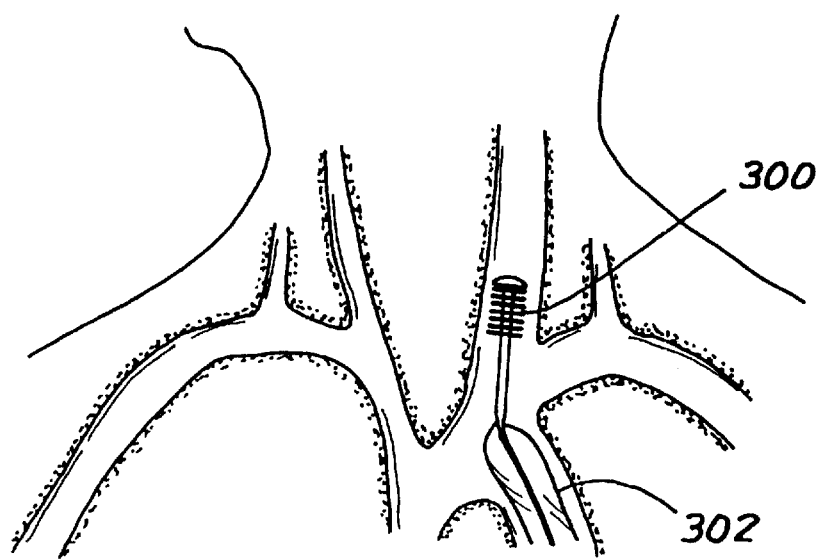
Fig. 19
Fig. 20
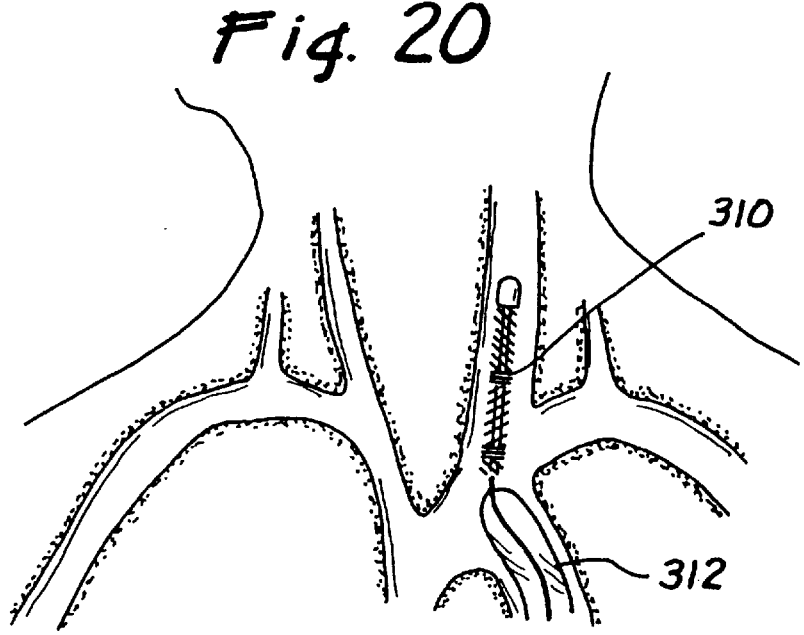

HEAT EXCHANGE CATHETER WITH IMPROVED INSULATED REGION

FIELD OF THE INVENTION

This invention relates generally to thermal probes or catheters and more particularly to probes or catheters having a) a heat transmitting core (e.g. a core comprising a heated element, a lumen for transmission of hot or cold fluid, or a circuit for the circulation of hot or cold heat transfer fluid), and b) insulation on the portion of the catheter that is inserted to insulate the heat transmitting core from the portion of the patient's body adjacent the insulation. The invention also relates to methods of use of such probes or catheters.

BACKGROUND OF THE INVENTION

When a catheter or probe is inserted into a patient, it is generally desirable to have a catheter of the lowest possible diameter. If the probe or catheter is inserted into the body via an existing body orifice, such as the urethra or vagina, the acceptable diameter of the catheter is dictated by the diameter of the body orifice. On the other hand, if the probe or catheter is inserted into the body via a percutaneous puncture site or incision, as is the case in percutaneous vascular catheters or catheters inserted through a sheath or trocar during minimally invasive surgery, the acceptable diameter is dictated by the acceptable size of the percutaneous puncture site or incision. In such cases, a smaller puncture site or incision is generally preferable to a larger puncture site or incision.

In certain medical procedures, it is desirable to place a catheter into the body with a region that is at a different temperature than that of the surrounding body tissue. For example, in some medical procedures it is desirable to place a probe or catheter having a heat exchanger (e.g., a heatexchange surface or balloon) that is either hotter or colder than the surrounding blood, into a body lumen such as a blood vessel of a patient such that the heat exchanger will effect warming or cooling of either the blood flowing through the vessel or the tissues adjacent thereto such as the vessel wall.

Heat exchanging catheters may be used to exchange heat with the blood, for example, to remove heat from the blood to induce whole body or regional hypothermia for the purpose of treating, or minimizing the adverse effects of certain neurological diseases or disorders such as head trauma, spinal trauma and hemorrhagic or ischemic stroke. Additionally, it is sometimes desirable to induce whole body or regional hypothermia for the purpose of facilitating or minimizing adverse effects, such as neuronal damage, of certain surgical or interventional procedures such as open heart surgery, aneurysm repair surgeries, endovascular procedures, spinal surgeries, or other surgeries where blood flow to the brain, spinal cord or vital organs may be interrupted or compromised. Hypothermia has also been found to be advantageous to protect cardiac muscle tissue during and/or after myocardial ischemia and is protective of other tissues such as kidney or liver tissue.

Neural tissue such as the brain or spinal cord, is particularly subject to damage by vascular disease processes including, but not limited to ischemic or hemorrhagic stroke, blood deprivation for any reason including cardiac arrest, intracerebral or intracranial hemorrhage, and head trauma. In each of these instances, damage to brain tissue may occur because of brain ischemia, increased intracranial pressure, edema or other processes, often resulting in a loss of cerebral function and permanent neurological deficits. Likewise, during surgical procedures, it is often impossible to avoid disrupting the blood supply to all or part of the brain or spinal cord. This ischemia, even if very localized or very temporary, may nonetheless result in very serious and permanent injury to the patient.

Hypothermia applied to the neural tissue is known to be very neuroprotective. Although the exact mechanism for neuroprotection is not fully understood, lowering the brain temperature is believed to effect neuroprotection through several mechanisms including, the blunting of any elevation in the concentration of neurotransmitters (e.g., glutamate) occurring after ischemic insult, reduction of cerebral metabolic rate, reduction of intracranial pressure (ICP), moderation of intracellular calcium transport/metabolism, prevention of ischemia-induced inhibitions of intracellular protein synthesis and/or reduction of free radical formation as well as other enzymatic cascades and even genetic responses including apoptosis. Thus intentionally induced hypothermia of the neural tissue may prevent damage to brain or other neurological tissue during surgery or as a result of stroke, intracerebral hemorrhage and trauma.

The mammalian body generally functions most efficiently at normothermia. Therefore maintaining hypothermia in a portion of the body such as the brain or heart while maintaining the temperature of the rest of the body at normothermia may provide for protection of the target tissue, e.g. neuroprotection of the brain or protection of the myocardium from ischemic damage, while allowing the rest of the body to function at normothermia. Therefore a device that would facilitate the regional application of temperature exchange would be highly advantageous.

U.S. Pat. No. 5,486,208 (Ginsburg) describes an intravascular heat exchange catheter that comprises an elongate catheter shaft having a discrete heat transfer region located near its distal end. In one embodiment described in this patent, the catheter is inserted into a blood vessel of the patient and heat exchange fluid is circulated through the catheter shaft to the heat transfer region. By heating or cooling the heat transfer region, heat is transferred to or from the blood that flows through the vessel past the heat transfer region of the catheter. In this manner, the tissue perfused by the blood may be increased or decreased, as desired, including in some instances the entire body of the patient. Although the heat transfer is intended to occur at the discrete heat transfer region, the heated or cooled fluid is circulated through the catheter shaft proximal to the heat transfer region and no separate insulator is included to deter or prevent heat transfer from occurring between the proximal portion of the catheter shaft and the patient's blood. Thus, even though the intended site of the heat transfer may be at the heat transfer region of the catheter, some unintended heat transfer could occur between the proximal catheter shaft and the patient's blood, depending on the difference in temperature between the heat transfer fluid and the patients blood, as well as the construction of the proximal catheter shaft.

U.S. Pat. No. 5,624,392 (Saab) describes a heat transfer catheter apparatus that comprises very thin-walled, high strength thermoplastic tubular material defining a plurality of lumens. At least two of the lumens are adjacent to each other and readily inflatable under fluid pressure and readily collapsible under vacuum. Fluid connection means are provided at or proximate to the distal ends of the two adjacent lumens, to define a continuous loop fluid containment and circulation system. Heat transfer fluid from a first (inlet) lumen is passed directly to a second (outlet) lumen such that a continuous flow of heat transfer fluid through the two lumens can be established and maintained. Because no separate insulator is described as being formed on the exterior of the proximal portion of the Saab catheter, unintended temperature exchange could occur between the proximal catheter shaft and the patients blood, depending on the difference in temperature between the temperature exchange fluid and the patient's blood, as well as the construction of the proximal catheter shaft.

Also, for example, U.S. Pat. No. 4,941,475 (Williams, et al.) describes a catheter that is useable to perform thermodilution cardiac output measurements. The thermodilution catheter described by Williams et al. comprises an elongate catheter shaft, a heat exchange balloon located on the catheter shaft, a lumen that extends from the proximal end of the catheter shaft to the heat exchange balloon, and a thermistor or sensor located distal to the balloon. A bolus of heated or cooled fluid is injected through the lumen and into the heat exchange balloon. Heat is thus added to or removed from the blood flowing past the heat exchange balloon and the thermistor or sensor is used to determine the rate of temperature change in the flowing blood. The patient's cardiac output is then computed on the basis of the rate of temperature change of the flowing blood. Although the temperature exchange with the blood is intended to occur only at the location of the heat exchange balloon, no insulator is provided on the catheter shaft proximal to the heat exchange balloon and, thus, depending on the difference in temperature between the temperature exchange fluid and the patient's blood, as well as the construction of the proximal catheter shaft, some unintended heat exchange could occur between the proximal catheter shaft and the patients blood or tissue. The unintended heat transfer to the blood at locations other than at the heat exchange balloon would affect the temperature of the blood in general, with possible adverse effects. In addition, maintaining the temperature of the heat exchange fluid at a maximum difference from the blood temperature is helpful in decreasing the noise to signal ratio and increasing the accuracy of the blood flow determination using this thermodilution catheter. Preventing the loss of heat to the blood would be very helpful in accomplishing this goal.

The desirability of providing some insulation on the exterior of the proximal shaft of a heat exchange catheter is addressed by U.S. Pat. No. 5,257,977 (Eschel), which describes a trans-urethral catheter useable to thermally treat prostate tissue. The catheter comprises an elongate catheter shaft, a discrete temperature exchange region, lumens that extend through the catheter shaft for circulating of heated fluid through the temperature exchange region and an insulator formed about the catheter shaft proximal to the temperature exchange region. The insulator comprises a multiplicity of sealed enclosures that contain trapped gas to decrease heat exchange between the heated liquid that is being circulated through the catheter shaft proximal to the heat exchange region and the surrounding wall of the urethra. However, the insulator of the Eschel catheter has a fixed diameter and results in an increase in the diameter of the proximal catheter shaft of the Eschel device.

Given the above-described desirability of minimizing the diameter of the insertion profile of the shaft of heat exchange catheters and probes during their insertion and advancement through blood vessels or other body lumens, but a simultaneous need for maximum thermal insulation of a heat exchange catheter or probe shaft after the catheter or probe is in place within the body of a patient, there exists a need in the art for the development of improved means for insulating portions of those heat exchange catheters or probes without requiring enlargement of the diameter of the catheter or probe during its insertion and advancement.

SUMMARY OF THE INVENTION

The present invention provides a heat exchange probe or catheter that generally comprises a) an elongate shaft having a proximal end and a distal end and a thermally-transmissive core; b) at least one heat exchange region formed on the elongate shaft, said heat exchange region having a tissue-contacting heat exchange surface through which heat may be exchanged between the thermally transmissive core and the adjacent body tissue (e.g., blood that flows past the heat exchange region); and c) an insulator disposed on the elongate shaft proximal to the heat exchange region, such insulator being initially disposed in a radially collapsed configuration and subsequently moveable to a radially expanded configuration. When in its radially expanded configuration, the insulator is effective to insulate the shaft to prevent exchange of heat between the thermally conductive core underneath the insulator and the patients blood or body tissue adjacent the exterior of the insulator.

In accordance with the invention, the insulator may comprise one or more inflatable balloons or bladders disposed about the elongate shaft proximal to the heat exchange region. For example, a plurality of elongate balloons may be disposed generally parallel to the elongate shaft so as to substantially surround the shaft and act to center the shaft between them when they are inflated. Alternatively, the insulated region may comprise a single large balloon that surrounds the shaft. The balloon may be provided with flexible attachments or other tethers extending between the shaft surface and the interior wall of the insulation balloon so that, when the insulating balloon is fully expanded, those attachments or tethers will hold the shaft in the approximate center of the insulating balloon.

Further in accordance with the invention, the insulator may comprise any suitable material, but preferably will comprise an inflatable, thin walled material that is relatively non-compliant, that is, will expand to a predictable diameter and then will not expand further, even if greater inflation pressure is applied. One such suitable material is polyethylene terepthalate (PET). Blood compatible insulation fluids, such as carbon dioxide or helium may be used to inflate the inflatable insulator, after the catheter has been inserted and advanced to its desired position within the patient's vasculature.

The heat exchange region of the catheter or probe may be formed on the elongate shaft. The thermally transmissive core of the elongate shaft may comprise one or more fluid circulation path(s) or lumen(s), whereby heated or cooled fluid may be passed into and/or extracted from the heat exchange region via the portion of the elongate shaft that is proximal to the heat exchange region. In embodiments where the thermally transmissive core comprises one or more fluid flow lumens, a heat exchange fluid may be circulated into or through the heat exchange region via such lumen(s).

BRIEF DESCRIPTION OF THE DRAWINGS

FIG. 3 is a longitudinal cross-sectional view of the proximal end of a catheter of the invention with the inflatable insulation region in a deflated condition.

FIG. 3A is a transverse cross-sectional view of a heat exchange fluid manifold of the catheter of the invention taken along line A—A in FIG. 3.

FIG. 3B is a transverse cross-sectional view of the heat exchange fluid manifold taken along line B—B in FIG. 3.

FIG. 3C is a transverse cross-sectional view of an insulation fluid manifold of the catheter of the invention taken along line C—C in FIG. 3.

FIG. 3D is a transverse cross-sectional view of an inflatable insulation region of the catheter of the invention, shown uninflated, and taken along line D—D in FIG. 3.

FIG. 4A' is a transverse cross-sectional view of an alternative embodiment of the inflatable region of the catheter of the invention, shown inflated, and again taken along line A—A in FIG. 4.

FIG. 5 is an elevational view of a heat exchange region of a catheter of the invention.

FIG. 5A is an elevational view of an alternative heat exchange region of the present invention.

FIG. 6 is an elevational view of a shaft portion of the catheter with the twisted heat exchange balloon seen in FIG. 5 removed.

FIG. 7 is an isolated view of the twisted heat exchange balloon of the catheter depicted in FIG. 5.

FIGS. 12A–12c are transverse cross-sectional views of the alternative heat exchange region of the catheter of FIG. 5A.

FIG. 15 is a schematic elevational view of a heat exchange catheter of the present invention inserted femorally and through the abdominal aorta of a patient so that a heat exchange region is located in one of the carotid arteries.

FIG. 15A is a detailed view of a heat exchange region of the catheter of FIG. 15 taken within the circle 15A.

FIG. 16 is a plan view of a segment of the heat exchange region of the catheter of FIG. 15.

FIG. 16A is a cross-sectional view of the heat exchange region of FIG. 16, taken along line 16A—16A.

FIG. 17 is a longitudinal cross-sectional view of a proximal manifold portion of the heat exchange region of the catheter of FIG. 15.

FIG. 17A is a transverse cross-sectional view of the heat exchange region taken along line 17A—17A of FIG. 17.

FIG. 17B is a transverse cross-sectional view of the heat exchange region taken along line 17B—17B of FIG. 17.

FIG. 17C is a transverse cross-sectional view of the heat exchange region taken along line 17C—17C of FIG. 17.

FIG. 18 is a longitudinal cross-sectional view of a proximal manifold portion of the heat exchange region of the catheter of FIG. 15.

FIG. 18A is a transverse cross-sectional view of the heat exchange region taken along line 18A—18A of FIG. 18.

FIG. 18B is a transverse cross-sectional view of the heat exchange region taken along line 18B—18B of FIG. 18.

FIG. 19 is a schematic elevational view of an alternative heat exchange region suitable for use with the heat exchange catheters of the present invention.

FIG. 20 is a schematic elevational view of another alternative heat exchange region suitable for use with the heat exchange catheters of the present invention.

DETAILED DESCRIPTION

The present invention provides a heat exchange catheter with an improved insulation region on the shaft of the catheter, which insulation region provides improved thermal insulation without significantly increasing the insertion profile of the catheter. Although the present invention is primarily intended to be used in the bloodstream with a catheter that cools blood flowing to specific locations in the patient's body to regulate the temperature of tissue at that location, those of skill in the art will readily appreciate that various other applications for the insulation region of the present invention are possible. Indeed, the present invention may have applications beyond controlling the temperature of tissue and circulating body fluid, and the claims should not be so limited.

In a preferred application, a catheter of the present invention is positioned within a patient's vasculature to exchange heat with the blood in order to regulate the overall body temperature, or to regulate the temperature of a localized region of the patient's body. The catheter of the present invention may be, for example, suitable for exchanging heat with arterial blood flowing toward the brain to cool the brain, and may thus prevent damage to brain tissue that might otherwise result from a stroke or other injury. Or the catheter may be used to cool venous blood flowing toward the heart to cool the myocardium and prevent tissue injury that might otherwise occur following a myocardial infarct (MI) or other similar event.

Figure 1:
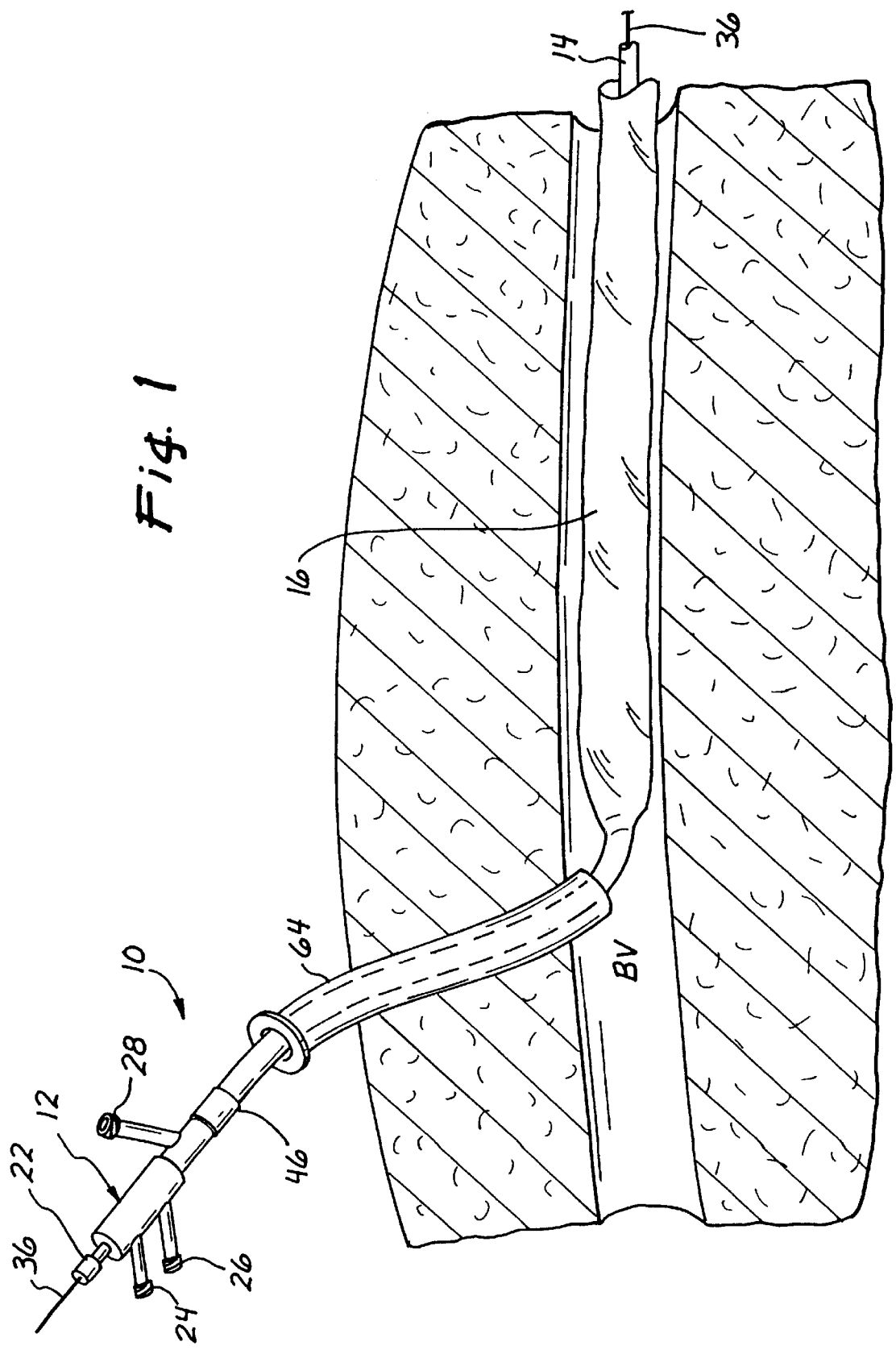
FIG. 1 is a cross section showing the catheter of the invention percutaneously inserted into a blood vessel.
Figure 2:
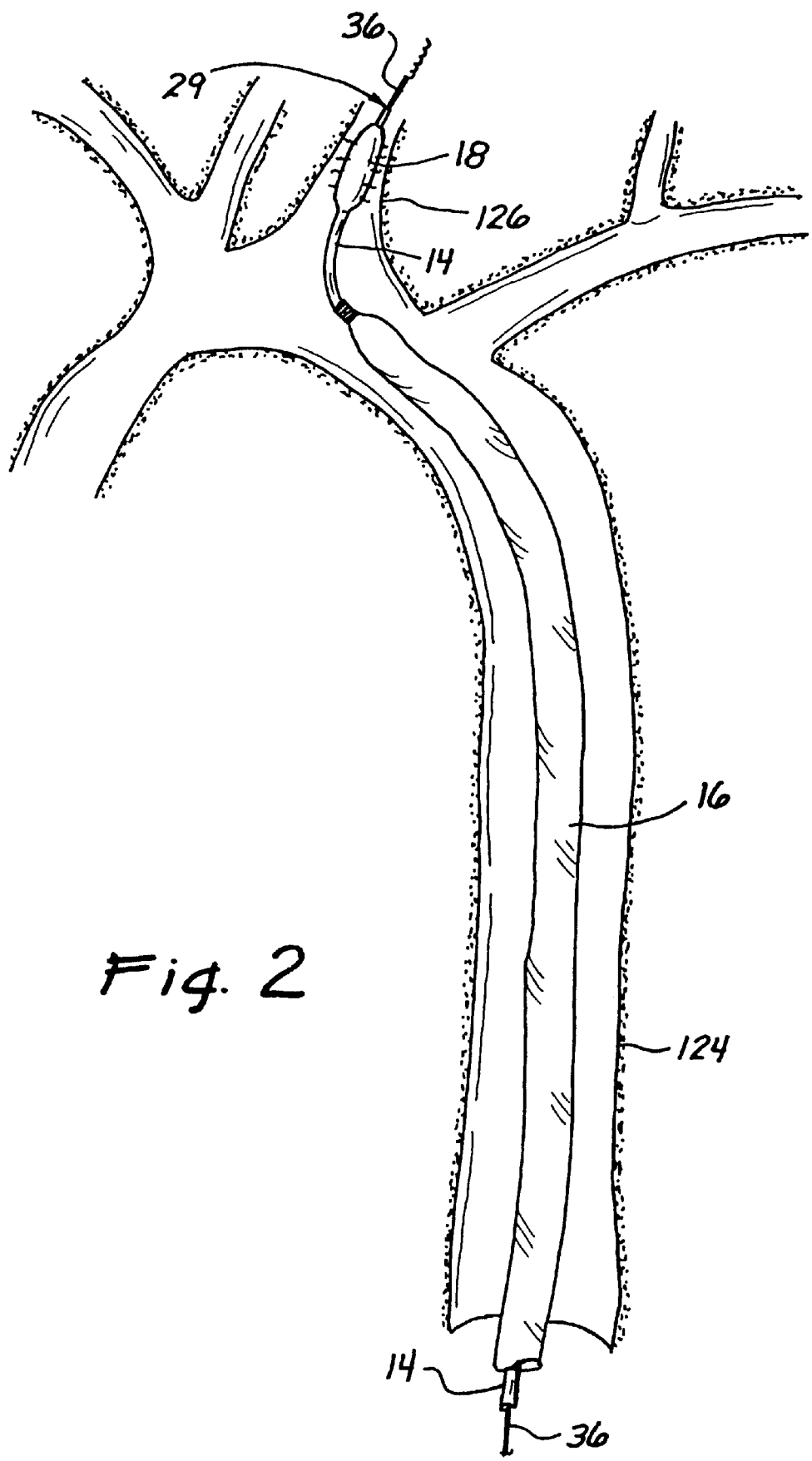
FIG. 2 is a drawing of the distal portion of the catheter with a heat exchange balloon located in the left common carotid artery.

Referring now to FIGS. 1 and 2, an exemplary embodiment of the heat exchange catheter 10 of the invention comprises a proximal hub 12, a shaft 14, an insulating sheath 16, a heat exchange region 18 which may be in the form of an inflatable balloon, and a distal tip 29. The hub 12 may include a working port 22, an inflow port 24, an outflow port 26, and an inflation port 28.

As seen in FIG. 3, a length of the proximal end of the catheter shaft 14 is contained within the hub 12. The hub 12 may be sealed around the shaft 14, such as by injection molding, or the shaft may be inserted into a bore formed through the hub. For example, the hub may be separately formed with a throughbore into which the shaft 14 inserts and is affixed with, for example, adhesives or thermal bonding. With reference to FIGS. 3A and 3B, the shaft 14 has three lumens running along its length to the distal tip 29: a working lumen 30, an inflow lumen 32 and an outflow lumen 34. The working port 22 communicates with the working lumen 30 so that the operator may insert items through the working port, through the working lumen and thus out the distal tip 29 of the catheter. For example, a guide wire 36 may be inserted into the working lumen 30 and out the distal tip 29 to guide the insertion of the catheter. Likewise, the working lumen 30 may be useful for injection of medicaments, insertion of a temperature probe, measurement of pressure, and the like.

For purposes of this description the inflow lumen is lumen 32, and the outflow lumen is 34. As one of skill in the art may readily appreciate, the direction of flow of the heat exchange fluid, as described below, may be reversed if desired by reversing the flow in the inflow and outflow lumens.

As seen in FIG. 2, the heat exchange catheter 10 of this embodiment has a heat exchange region 18, preferably in the form of a balloon, that receives heat exchange fluid from the inflow lumen 32 of the shaft 14. The heat exchange fluid circulates through the balloon interior and returns proximally along the shaft 14 through the outflow lumen 34. The heat exchange region 18, in conjunction with a shaft 14 of the configuration of the embodiment described herein, is illustrated in greater detail in FIGS. 5 through 14.

Figure 4:
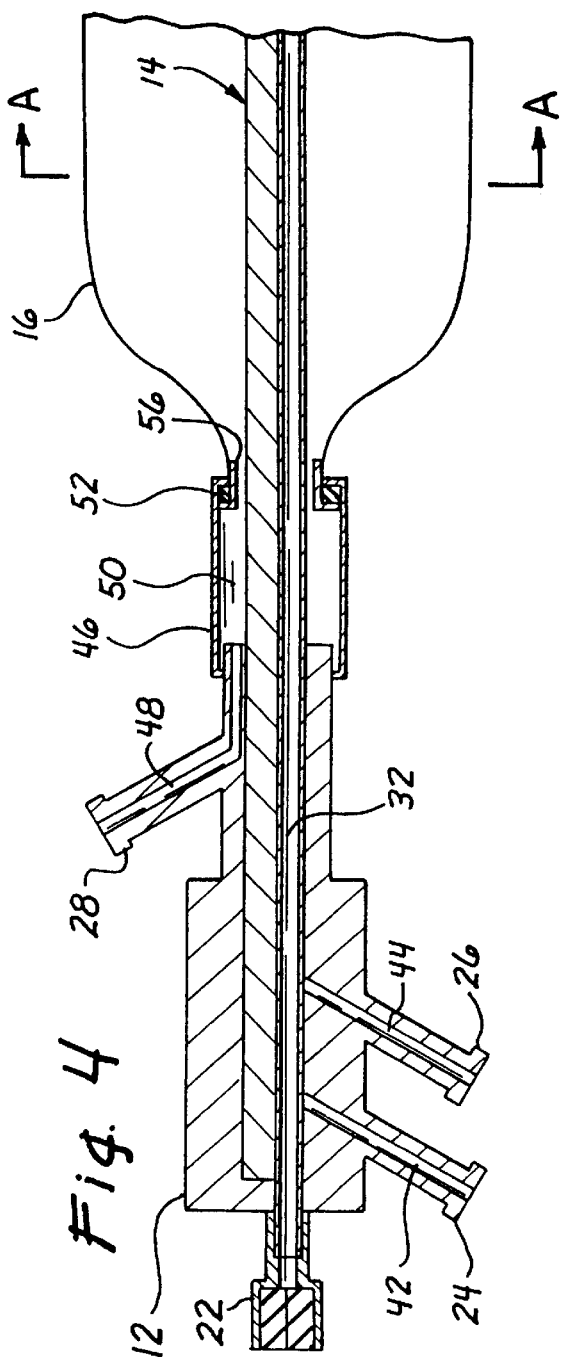
FIG. 4 is a longitudinal cross-sectional view of the proximal end of the catheter of the invention with the inflatable insulation region in an inflated condition.

An inflow channel 42 is formed through the inflow port 24 and hub 12, and an opening 38 (FIG. 3A) is formed in the wall of the inflow lumen in the portion of the shaft 14 contained within the hub. The inflow channel 42 is in fluid communication with inflow lumen 32 at the opening 38. Similarly, an outflow channel 44 is formed through the outflow port 26 and hub 12, and an opening 40 (FIG. 3B) is formed in the wall of the outflow lumen 34 in the portion of the shaft 14 contained within the hub. The outflow channel 44 is in fluid communication with the outflow lumen 34 at the opening 40. As seen in FIGS. 3 and 4, an inflation manifold 46 is located around the catheter shaft 14 distally with respect to the hub 12. An inflation channel 48 extends through the inflation port 28, and communicates with an interior space 50 of the inflation manifold 46. As seen in FIGS. 3 and 3C, a seal 52 is formed, for example by adhesive or potting compound, between the inflation manifold 46 and a coupling end 54 provided on the proximal end of the insulating sheath 16. The interior volume of the insulating sheath 16 is in fluid communication with the interior space 50 of the inflation manifold 46 so that an inflation medium such as $CO_2$ or Helium may be introduced through the inflation port 28 via the inflation channel 48 to inflate the insulating sheath. Consequently, the insulating sheath 16 may be expanded from an uninflated state (e.g., as seen at 16 in FIG. 3) by the introduction of an inflation medium, to an inflated state, as seen at 16 in FIG. 4.

Figure 4A:
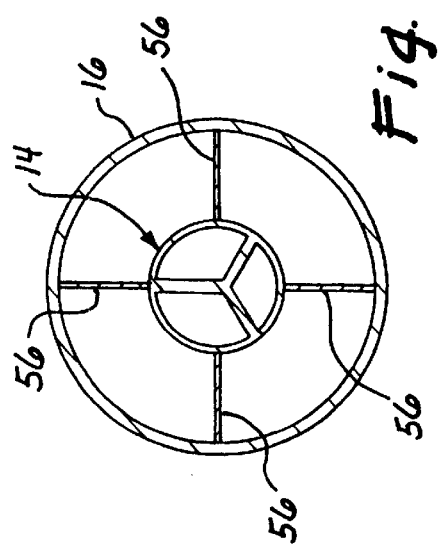
FIG. 4A is a transverse cross-sectional view of the inflatable insulation region of the catheter of the invention, shown inflated, and taken along line A—A in FIG. 4.
Figure 4A:
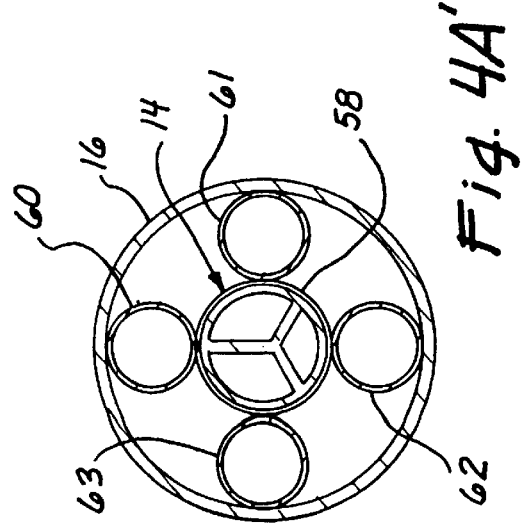

In some embodiments, various means may be provided to center the insulated portion of the shaft within the insulation sheath. As seen in FIGS. 3D and 4A, tethers 56 may be provided to attach the inner surface of the insulation sheath 16 to the outer surface of the shaft 14. When the insulation sheath 16 is fully inflated, these tethers 56 serve to generally center the shaft 14 within the insulating sheath. The centering function of the tethers 56 serves to maximize the overall insulating effect of the inflated sheath 16 by keeping the shaft 14 as far away from the walls of the sheath as possible, thus ensuring that the shaft will have the maximum insulated distance at all points along its length. For example, when the insulated shaft 14 is located in a blood vessel with flowing blood, the outside of the insulating sheath 16 is in thermal contact with the blood, and a uniform insulating gap is provided concentrically surrounding the shaft 14. Alternatively, the centering elements 56 may be collapsible stand-offs attached to the outer surface of the shaft 14 to hold the inflated sheath 16 away from the shaft and thereby center the shaft within the insulating sheath.

Another method of centering the shaft 14 within the insulating sheath employs a structure with multiple thin-walled tubes surrounded by the sheath 16, said tubes readily inflatable under pressure and collapsible under vacuum. This construction is depicted in FIG. 4A'. A central thin-walled tube 58 large enough to accommodate the shaft 14 is surrounded by a plurality of internal tubes 60, 61, 62, 63. When all the lumens defined by the internal tubes 60, 61, 62, 63 are inflated, they hold the insulating sheath 16 around the shaft 14 at a uniform distance approximately equal to the diameter of the internal lumens. In this way the shaft 14 is centered within the insulating sheath.

Any number of heat exchange probes or catheters may utilize the expandable insulation of this invention. One example of a catheter for such use is shown and described in relation to FIGS. 5 through 14 inclusive.

Figure 11:
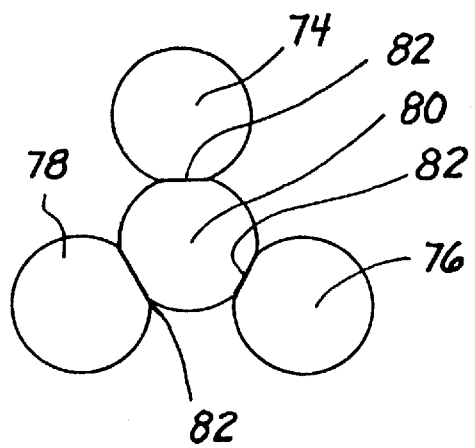
FIG. 11 is a transverse cross-sectional view of the twisted heat exchange balloon taken along line 11—11 in FIG. 7.
Figure 12:
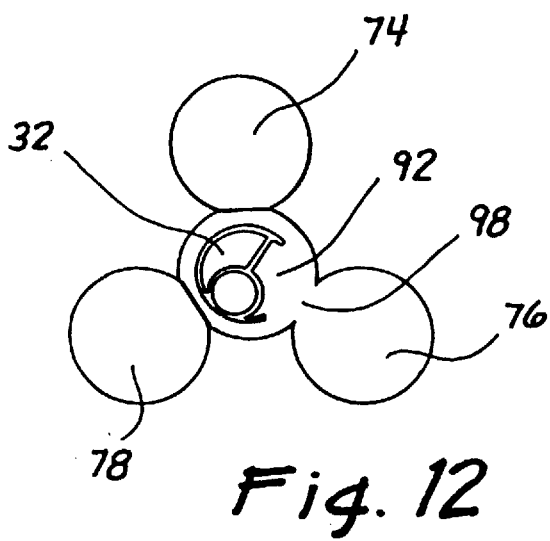
FIG. 12 is a transverse cross-sectional view of a proximal section of the heat exchange region of the catheter taken along line 12—12 in FIG. 5.

As seen in FIGS. 5 and 7, the assembled catheter 10 has an exemplary heat exchange region 18 in the form of a four-lumen, thin-walled balloon 70 which is attached over the distal portion of the catheter shaft 14. The cross-sectional view of the four-lumen balloon 70 is shown in FIG. 11. The balloon has three elongated lobes that define outer lumens 74, 76, 78 and are wound in a helical pattern around an inner lobe defining an inner lumen 80. All four lumens are defined by the lobes of a thin walled balloon (and can be viewed as four separate balloons), and each outer lumen 74, 76, 78 shares a common thin wall segment 82 with the inner lumen 80. When installed, both the proximal end 84 and the distal end 86 of the balloon 70 are sealed around the shaft in a fluid tight seal.

Over the proximal length of the catheter, between the hub 12 and the proximal balloon attachment 84, the shaft 14 is at the extruded outer diameter of about 0.118 inches. The internal configuration is as shown for example, in cross-section 3D or in the shaft as shown in FIG. 4A. Immediately proximal of the balloon attachment 84, the shaft 14 is necked down at 88. The outer diameter of the shaft 14 is reduced to about 0.10 to 0.11 inches, but the internal configuration of the lumens is maintained. Compare, for example, the shaft cross-section of FIG. 10 with the cross-section shown in FIG. 12. This length of reduced diameter shaft 14 remains at approximately constant diameter of about 0.10 to 0.11 inches between the necked down location at 88 and a further necked down location at 90 (FIG. 6).

On the necked down location 88, a proximal balloon marker band 91 is attached around the shaft 14. The marker band is a radiopaque material such as a platinum or gold band or radiopaque paint, and is useful for locating the proximal end of the balloon 70 by means of fluoroscopy while the catheter is within the body of the patient.

At the marker band 91, all four lobes of the balloon 70 are reduced down and are fastened to the inner member at 84 (see FIG. 5). This may be accomplished by folding the balloon 70 down around the shaft 14, placing a sleeve, for example a short length of tubing, over the balloon and inserting adhesive, for example by wicking the adhesive, around the entire inner circumference of the sleeve. This simultaneously fastens the balloon 70 down around the shaft 14, and creates a fluid tight seal at the proximal end of the balloon.

Distal of this seal, under the balloon 70, a series of axially-spaced windows 92, 94, 96 is cut through the wall of the outflow lumen 34 in the shaft 14, as seen in FIG. 6. Juxtaposed to these windows, groups of slits 98, 100, 102 are cut into the wall of the outer balloon lumens 74, 76, 78, respectively. Because the outer tubes having the outer lumens 74, 76, 78 are twined about the shaft 14 in a helical fashion, each of the outer lumens passes over a generatrix of the shaft adjacent the outflow lumen 34 of the shaft at a slightly different axial location. Therefore, where each outer lumen 74, 76, 78 passes over the outflow lumen 34, one of the windows 92, 94, 96 is registered with one of the groups of slits 98,100, 102 to fluidly connect the proximal portion of the respective outer lumens 74, 76, 78 to the outflow lumen of the shaft 14.

Alternatively, as shown in FIGS. 5A and 12A–12C, an elongate window 92' may be cut through the wall of the outflow lumen 34'. As shown in FIGS. 12A–12C an annular space 91' surrounds the shaft 14' within the inner lobe of the balloon 70' that forms the inner lumen 80'. Along the portion of the balloon over the proximal shaft that includes the elongate window 92', five groups of slits 98', 100' and 102' are cut into the common wall between each of the outer balloon lumens and the inner lumen 80'. Because the outer lumens 74', 76', 78' are twined about the inner lumen 80' in a helical fashion, each of the outer tubes passes over the outflow lumen of the inner shaft member at a slightly different location along the length of the inner shaft. The elongate window 92' is sufficiently long that each of the outer lumens passes 74', 76', 78' over the elongate window at a point where at least one slit from each group of the slits 98', 100' and 102' is cut into the common wall (as depicted in the cross-sections 12A–12C). The other slits open into the space 91' which, in turn, is in fluid communication with the outflow lumen 34'. In this way each of the outer lumens 74', 76', 78' is in fluid connection with the outflow lumen 34' over a relatively short distances of the balloon, either directly through a slit over the elongate window 92', or via the annular space 91'. FIG. 5A shows the slits in all the exterior balloon lobes as being formed along the same linear axis over the window 92', but it will be readily perceived that the windows may be staggered around the balloon so that they are formed along a shorter length of the balloon, for example 2 cm. Desirably, because of the length of the window 92' and the pitch of the twisted lobes, at least one of the slits in each group will be positioned directly over the window.

Figure 13:
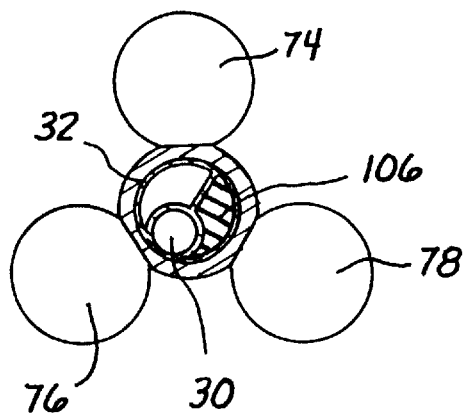
FIG. 13 is a transverse cross-sectional view of a mid-section of the heat exchange region of the catheter taken along line 13—13 of FIG. 5.
Figure 14:
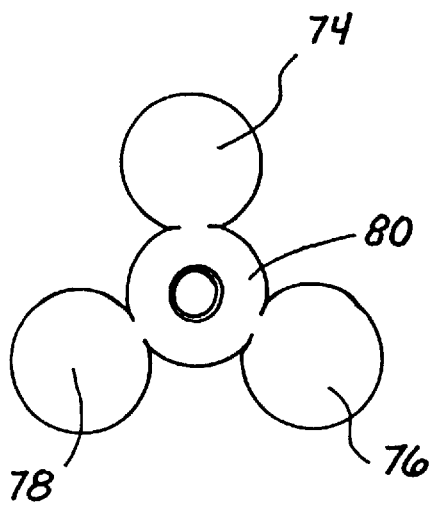
FIG. 14 is a transverse cross-sectional view of a distal section of the heat exchange region of the catheter taken along line 14—14 of FIG. 5.

Distal of the windows 92, 94, 96 in the outflow lumen 34, the tube defining the inner lumen 80 of the four-lumen balloon 70 is sealed around the shaft 14 in a fluid tight seal, as indicated in FIG. 5 at 104. The outflow lumen 34 is thereafter plugged as seen at 106, and the inflow lumen is open to the inner lumen 80. (See FIG. 13.) As shown in FIG. 13, this may be accomplished by necking down the shaft 14 to seal the outflow lumen shut at 106, removing the wall of the inflow lumen 32, piercing a small hole in the wall of the inner lumen at 110, wicking UV curable adhesive into the hole and around the entire outside of the shaft, and then curing the adhesive to create a plug 111 about the wall of the shaft 14. This adhesive plug serves to prevent the portion of the inner lumen proximal to the plug 111 from being in fluid communication with the inner member distal to the plug.

With reference to FIG. 6, the guide wire lumen 30 of the shaft may be terminated and joined to a guide wire tube 112 at a location just distal of the necked down location 90. The distal end 86 of the balloon 70 including all four lumens of the balloon is sealed down around the guide wire tube 112 in a manner similar to the way the balloon is sealed at the proximal end 84 around the shaft 14. This seals all four lumens of the balloon 70 in a fluid tight seal. Just proximal of the seal, slits 116 (FIGS. 5 and 7) are cut into the common wall between each of the three outer lumens 74, 76, 78 of the balloon 70 and the inner lumen 80 so that each of the outer lumens is in fluid communication with the inner lumen. (See FIG. 9 and FIG. 14.) In this way, the inflow lumen 32 is open into the inner lumen of the four-lobed balloon 70 and the inner lumen in turn is in fluid communication with the distal ends of each of the three outer lobes.

Just distal of the balloon 70, near the distal seal, a distal marker band 118 is placed around the guide wire tube 112. A flexible length of tube 120 may be joined onto the distal end of the guide wire tube 112 to provide a flexible tip to the catheter 10. The distal end 29 of the flexible tube 120 is open so that a guide wire may exit the tip, or medicine or radiographic fluid may be injected distal of the catheter through the working lumen.

In use, the catheter 10 is inserted into the patient, for example, percutaneously into a blood vessel BV by the well known Seldinger technique. The catheter 10 may be directly inserted, or may be inserted through an introducer sheath 64 (FIG. 1). In order to minimize the diameter of the catheter, the catheter is inserted with the insulating sheath 16 in an uninflated condition (FIG. 3). When the catheter is in place, the insulating sheath 16 may be inflated (FIG. 4) with a suitable inflation fluid, for example with a biocompatible gas such as $CO_2$ or Helium. A suitable inflation medium will be any fluid that is provides adequate insulation, is non-toxic, and generally will dissolve in blood so that, should a leak occur in the insulating balloon, the escaping gas will dissolve in the blood and be expelled through the lungs and will not form harmful bubbles in the blood stream.

The gap formed between the insulating sheath 16 and the shaft 14 provides excellent thermal insulation, and the tethers 56 (FIG. 4A) or tubes 60, 61, 62, 63 (FIG. 4A') center the shaft within the inflated insulated region. Preferably, the inflation fluid will be maintained within the insulating sheath 16 at relatively low pressures. The portion of the insulating sheath 16 that is within the introducer sheath 62 or the incision will not fully inflate at the relatively low pressures that are used, though the inflation medium will be permitted to pass through such narrowed regions. The inflation pressure should be sufficient to fully inflate the portion of the insulating sheath that is within the blood vessel against normal blood pressures, and sufficient pressure to flow through the sheath or incision to inflate the sheath, but no greater so that if there is a rupture, only a minimal amount of inflation medium will be introduced into the blood stream. In an exemplary embodiment, the inflation pressure should be no more than 2 psi above blood pressure in the vessel in which it is located. Additionally, the inflation source desirably has a flow restrictor that limits inflow of inert gas to the interior of the insulation region to a rate similar to the rate the gas would be absorbed by the body, e.g., 2 cc/min to 3 cc/min if the inflation medium is $CO_2$.

Figure 9:
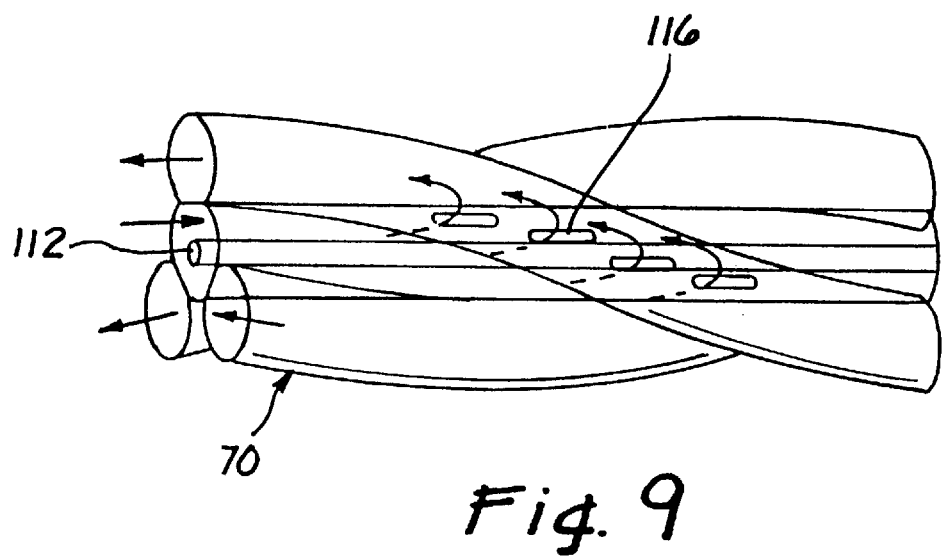
FIG. 9 is a detailed view of a distal section of the heat exchange region of the catheter taken within the circle 9 in FIG. 5.
Figure 10:
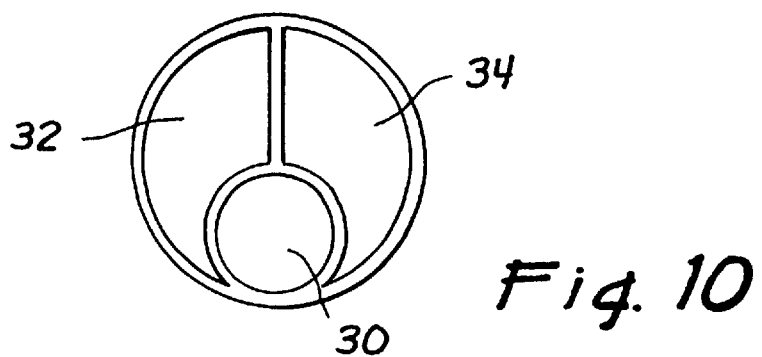
FIG. 10 is transverse cross-sectional view of the shaft of the catheter taken along line 10—10 in FIG. 6.

The catheter is inserted into the body of a patient so that the balloon 70 is within a blood vessel BV. Heat exchange fluid is circulated into the inflow port 24, travels down the inflow lumen 32 and into the inner lumen 80 of the four-lumen balloon 70. The heat exchange fluid travels to the distal end of the inner lumen 80 and then through the slits 116 between the inner lumen 80 and the outer lumens 74,76,78, as depicted in FIG. 9.

Figure 8:
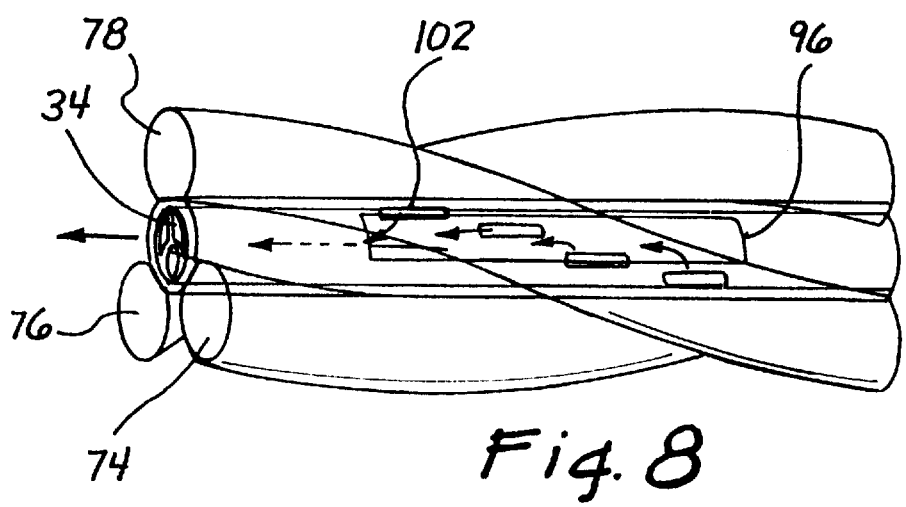
FIG. 8 is a detailed view of a proximal section of the heat exchange region of the catheter taken within the circle 8 in FIG. 5.

The heat exchange fluid then travels back through the three outer lumens 74, 76, 78 of the balloon 70 to the proximal end of the balloon in a helical flow pattern. At some point along the proximal portion of the shaft, each outer lumen is located over the portion of the shaft having a window 92, 94, 96 to the outflow lumen 34 and the outer balloon lumens have slits 98, 100, 102 that are aligned with the windows. The heat transfer fluid passes through the slits 98, 100, 102 through the windows 92, 94, 96 and into the outflow lumen 34. For instance, FIG. 8 shows fluid passing from the lumens 74, 76, 78 through slits 102 and window 96 into outflow lumen 34. From there it is circulated out of the catheter through the outflow port 26.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral artery, through the aorta and then into the left common carotid, the blood flow in the left common carotid would be flowing past the heat exchange region of the catheter in a direction from the proximal to the distal part of the heat exchange region. It would be most efficient in this situation to have the heat exchange fluid in the outer balloon lumens flowing from the distal end toward the proximal end, as described above and shown in the figures. It is to be readily appreciated, however, that if the balloon were placed so that the blood was flowing along the catheter in the direction from distal to proximal, such as, for example, if the heat exchange region was placed into the inferior vena cava with a jugular insertion, it would be desirable to have the heat exchange fluid circulate in the outer balloon lumens from the proximal end to the distal end. This could be accomplished by merely reversing which port is used for the inflow direction and which for the outflow.

Where it is important that the heat exchange medium, for example heat exchange fluid, be carried to the heat exchange region with as little heat exchange along the way as possible, thermal insulation along that length of the catheter shaft is particularly helpful. This may be true if a regional heating or cooling effect is desired, as would be the case with regional cooling of the brain as described below, or if the tissue between the insertion point and the heat exchange region needed to be protected from temperature exchange with the shaft. An example of the lafter situation is where very hot fluid is transmitted to the heat exchange region, as might be the case with heated balloon angioplasty, a thermodilution procedure, or thermal ablation at the heat exchange region. In such situations, an inflatable insulation region along the catheter length would be particularly desirable.

In particular, the heat exchange catheter 10 of the present invention is useable to perform regional percutaneous temperature regulation (rPTR™) (the acronym rPTR is a trademark of Radiant Medical, Inc. of Redwwod City, Calif.). Such rPTR™ procedure is accomplished by percutaneously inserting the catheter 10 into a blood vessel and advancing the catheter 10 through the patient's vasculature until its heat exchange region 18 is positioned within or slightly upstream of the particular region of the body that is to be heated or cooled. A heated or cooled heat exchange medium is infused through the catheter shaft 14 to the heat exchange region 18. During such infusion of the heat exchange medium, insulating sheath 16 is deployed or utilized to minimize heat exchange between the catheter shaft 14 proximal to the heat exchange region 18 and the patient's blood flowing thereby. In this manner, effectve heat exchange with the patient's blood occurs only at the heat exchange region 18 of the catheter 10.

Such devices where the inflatable insulating sheath of this invention would be particularly advantageous would be, for example, in heat exchange catheters intended to provide directed cooling to a patient's brain. Such a catheter might be constructed as shown in FIGS. 15–20. Other catheters where the inflatable insulating sheath of this invention would be particularly advantageous are disclosed in U.S. Pat. No. 5,957,963 to Dobak, III, and in WO 99/48449, both assigned to Del Mar Medical Technologies, Inc.

The magnitude of heat exchange is a function of the difference between the temperature of the blood flowing past the heat exchange region and the temperature of the surface of the heat exchange elements, a difference that may be described as $\Delta T$. If cooled (or heated) blood is to be directed to a specific location in the patient, the greatest $\Delta T$ must be maintained between the heat transfer region and the blood that subsequently flows to that region.

In the case of directing the cooled blood to the patient's brain, the heat transfer catheter may be inserted into the leg or abdominal region and advanced through the vasculature, forexample up the aorta 124, to the carotid artery 126. This general configuration is shown if FIG. 2. The heat transfer region 18 is placed essentially entirely into the carotid artery. Heat transfer fluid is circulated from outside the patient, up the shaft 14, to the heat transfer region 18, and then back down the shaft and out of the body. The desired effect is to cool blood directed through the carotid to the brain and thus cool the brain. All heat transferred to the heat exchange medium in the shaft 14 from the blood in the aorta 124 would affect primarily blood being carried away from the head and would not serve to cool the brain. In fact, where the operator desires to maintain normothermia in the rest of the body while cooling only the brain, this lost heat would serve to undesirably cool the rest of the body. Not only would the heat transferred in the aorta serve to cool the rest of the body and not the brain, but it would simultaneously decrease the cooling effect directed to the brain by increasing the temperature of the heat exchange fluid and thus decreasing the $\Delta T$ between the heat exchange region and the blood of the patient.

An effective insulating member along the catheter shaft may prevent undue thermal exchange between the heat exchange fluid proximal ofthe heat exchange region, and thus ensure the maximum $\Delta T$ between the heat exchange region and the patient's blood. However, most truly effective thermal insulation available prior to the invention are sufficiently bulky to unacceptably increase the diameter of the catheter assembly prior to insertion so that percutaneous insertion into a small incision or through a small conduit such as a sheath trocar or body orifice, is not feasible. In contrast, the inflatable insulation of the invention could be inserted in its uninflated state into a body cavity such as a blood vessel, the peritoneal cavity, the bladder or the like through an incision or conduit that is significantly smaller in diameter than the cavity, inflated after insertion, and provide effective insulation. In this way, maximum temperature differential between the heat exchange region and the target tissue may be maintained while avoiding unwanted heat exchange between the shaft and the tissue that may be in contact with the shaft region. Desirably, the insertion channel, be it formed by a percutaneous incision or puncture or by a trocar or introducer, for example, is preferably 9 French or less in size, but may be larger, for example as large as 13 French.

FIGS. 15–20 illustrate various heat exchange regions suitable for use with catheters of the present invention. In particular, the heat exchange regions shown can be provided on the distal portion of a heat exchange catheter, wherein an insulating region is provided on a proximal portion, or along the entire proximal length of the catheter that is within the body.

For example, FIGS. 15 and 15A illustrate a heat exchange catheter 200 inserted through one of the femoral arteries and advanced until a heat exchange region 202 is located within one of the carotid arteries of the neck. The catheter 200 comprises the heat exchange region 202 on a distal end, an elongate insulating region 204 located proximally thereto, and an inner shaft 206 extending substantially the entire length of the catheter. The catheter 200 passes into the body through an introducer 208 and includes a proximal hub 210. The heat exchange region 202 is connected to the shaft 206, as best 20 seen in FIG. 15A. Heat is transferred to and from the heat exchange region 202 via the shaft 206, and the insulating region 204 helps improve the efficiency of the device by inhibiting heat transfer between the vasculature and the shaft 206.

In a preferred embodiment, heattransferfluid circulates to and from the heat exchange region 202 via channels formed in the shaft 206. FIGS. 16 and 16A illustrate one exemplary embodiment of a heat exchange region 202 comprising a plurality of tubular members that are stacked in a helical plane. More specifically, a central tube 220 defines a central lumen 222 therewithin. A pair of smaller intermediate tubes 224a, 224b attaches to the exterior of the central tube 220 at diametrically opposed locations. Each of the smaller tubes 224a, 224b defines a fluid lumen 226a, 226b therewithin. A pair of outer tubes 228a, 228b attaches to the exterior of the intermediate tubes 224a, 224b in alignment with the aligned axes of the central tube 220 and intermediate tubes 224a, 224b. Each of the outer tubes 228a, 228b defines a fluid lumen 230a, 230b within. By twisting the intermediate and outer tubes 224a, 224b, 228a, 228b around the central tube 220, the helical ribbon-like configuration of FIG. 16 is formed.

An inflow path of heat exchange medium is provided by the central tube 220, as described in greater detail below. The intermediate tubes 224a, 224b and outer tubes 228a, 228b define a fluid outflow path within the heat exchange region 202. Heat exchange fluid is transferred into the catheter 200 through an inflow port 240 of the hub 210, as seen FIG. 15, and is removed from the catheter 200 through an outflow port 242. A working lumen port 244 is also provided on the hub 210.

Now with reference to FIGS. 17 and 17A–17C, a proximal manifold of the heat exchange region 202 will be described. The shaft 206 extends a short distance, desirably about 3 cm, within the central tube 220 and is thermally or adhesively sealed to the interior wall of the central tube as seen at 250. As seen in FIG. 17A, the shaft 206 includes a planar bulkhead 252 that generally evenly divides the interior space of the shaft 206 into an inflow lumen 254 and an outflow lumen 256. A working or guidewire lumen 260 is defined within a guidewire tube 262 that is located on one side of the shaft 206 in line with the bulkhead 252. Desirably, the shaft 206 is formed by extrusion. The outflow lumen 256 is sealed by a plug 264 or other similar expedient at the terminal end of the shaft 206. The inflow lumen 254 remains open to the central lumen 222 of heat exchange region 202. The guidewire tube 262 continues a short distance and is heat bonded at 270 to a guidewire extension tube 272 generally centered within the central tube 220.

A fluid circulation path is illustrated by arrows in FIG. 17 and generally comprises fluid passing distally through the inflow lumen 254 and then through the entirety of the central lumen 222. Fluid returns through the lumens 226a, 226b, and 230a, 230b of the intermediate and outer tubes 224a, 224b, and 228a, 228b, respectively, and enters reservoirs 274 and 275. Alternatively, two windows may be formed 276 and a counterpart not shown in FIG. 17 one helical twist farther down the shaft, between each side of the twisted ribbon (i.e., lumens 224a and 224b on one side, and 228a and 228b on the other side). in this way, one reservoirfrom each side of the twisted ribbon is formed in fluid communication with the outflow lumen 256 (configuration not shown). Fluid then enters the outflow lumen 256 through apertures, e.g., 276, provided in the central tube 206 and a longitudinal port 278 formed in the wall of the shaft.

A distal manifold of the heat exchange region 202 is shown and described with respect to FIGS. 18 and 18A–18B. The outer tubes 228a, 228b taper down to meet and seal against the central tube 220 which, in turn, tapers down and seals against the guidewire extension tube 272. Fluid flowing distally through the central lumen 222 passes radially outward through a plurality of apertures 280 provided in the central tube 220. The apertures 280 open to a distal reservoir 282 in fluid communication with lumens 226a, 226b, and a distal reservoir 281 in fluid communication with lumens 230a, 230b of the intermediate and outer tubes 224a, 224b, and 228a, 228b.

With this construction, heat exchange fluid introduced into the input port 240 will circulates through the inflow lumen 254, into the central lumen 222, out through the apertures 280, and into the distal reservoir 282. From there, the heat exchange fluid will travel proximally through both intermediate lumens 226a, 226b and outer lumens 230a, 230b to the proximal reservoirs 274 and 275. Fluid then passes radially inwardly through the apertures 276 and port 278 into the outflow lumen 256. Then the fluid circulates back down the shaft 206 and out the outlet port 242.

The twisted ribbon configuration of FIGS. 15–18 is advantageous for several reasons. First, the relatively flat ribbon does not take up a significant cross-sectional area of a vessel into which it is inserted. The twisted configuration further prevents blockage of flow through the vessel when the heat exchange region 202 is in place. The helical configuration of the tubes 224a, 224b, 228a, 228b also aids to center the heat exchange region 202 within a vessel by preventing the heat exchange region from lying flat against the wall of the vessel along any significant length of the vessel. This maximizes heat exchange between the lumens and the blood flowing next to the tubes. Because of these features, the twisted ribbon configuration is ideal for maximum heat exchange and blood flow in a relatively small vessel such as the carotid artery. As seen in FIG. 16A, an exemplary cross-section has a maximum diameter of about 5.9 mm, permitting treatment of relatively small vessels.

In any configuration, for maximum heat exchange results, it is important that the difference in temperature between the blood and heat exchange region be as large as possible. Because of the long length of catheter required for selective cooling of the brain within the carotid artery in conjunction with femoral insertion, maximum thermal insulation of the shaft is important to maximize heat transfer with the blood flowing to the brain and minimize heat transfer with the blood flowing away from the brain. Because the catheter is passed through the abdominal aorta, which is relatively large, there is room within this artery to utilize an inflatable insulating region 204 as previously described. Because the insulating region 204 is first deflated, the incision or puncture into the arterial system is minimized.

Other heat exchange regions suitable for use with catheters of present invention are seen in FIGS. 19 and 20. In FIG. 19, a flexible metal heat exchange region 300 comprises a bellows configuration with a convoluted surface having heat exchange fins in the shape of annular folds. The annular folds are desirably hollow and receive circulating heat exchange fluid within. Again, the effectiveness of the heat exchange region 300 is enhanced with the use of an insulating region 302 surrounding the catheter shaft. In FIG. 20, a flexible metal heat exchange region 310 comprises a hollow metal element having spiral heat exchange fins on the external surface. A co-axial central tube (not shown) delivers heat exchange fluid into an inner space of the heat exchange region 310. Again, an insulating member 312 surrounds the shaft of the exchange catheter for maximum efficiency.

While a particular embodiment of the invention has been described above, for purposes of illustration, it will be evident to those skilled in the art that numerous variations of the details may be made without departing from the invention as defined in the appended claims. By way of example and not limitation, the heat transfer fluid could be a liquid or a gas, the heat transfer region could be in the forrn of a balloon, a flexible metallic member, a region with multiple discrete heat exchange members or the like, all without deviating from the spirit of this invention. Similarly other-variations of the embodiments described are anticipated within the scope of the invention as claimed.

What is claimed is:

1. A beat exchange catheter adapted to pass through the body to a target location, comprising:
   A an elongate shaft having a proximal end and a distal end;
   B a heat exchange region disposed on the shaft adapted to exchange heat with a body fluid or tissue at the target location; and,
   C an elongate insulating region disposed about a substantial portion of the shaft that is proximal to the heat exchange region, the insulating region providing a thermal barrier between said substantial portion of the shaft and the body, the insulating region being radially expandable from a first size to a second size larger than the first size, said first size being suitable for insertion of the catheter through a channel into the body.

2. A catheter as in claim 1 wherein the body fluid or tissue comprises blood, and wherein the catheter is adapted to be inserted into a parient's vasculature.

3. A catheter as in claim 1 further including a fluid flow path in the shaft for the flow of heat exchange fluid from the proximal end of the shaft to the heat exchange region.

4. A catheter as in claim 3 wherein said fluid flow path comprises a circulation loop.

5. A catheter as in claim 4 wherein the heat exchange region is a balloon having an interior volume and an exterior surface, wherein said interior volume is in fluid communication with said circulation loop and said exterior surface is in contact with the body fluid or tissue to change the temperature of the body fluid or tissue.

6. A catheter as in claim 1 wherein said heat exchange region is a balloon.

7. A catheter as in claim 6 wherein said balloon comprises a plurality of longitudinally extending tubes defining flow lumens, and further including a fluid flow path in the shaft for the flow of heat exchange fluid, the heat exchange region further including a manifold fordelivering heat exchange fluid from the fluid flow path to a distal end of each of the flow lumens.

8. A catheter as in claim 7 wherein at least some of the longitudinally extending tubes extend in a helical configuration.

9. A catheter as in claim 1 wherein said heat exchange region is further constructed to perform a procedure selected from the group consisting of ablation, angioplasty, thermodilution, whole body temperature regulation, and regional temperature regulation.

10. A catheter as in claim 1 wherein the insulation region comprises a non-compliant balloon inflatable from said first size to said second size.

11. A catheter as in claim 10 wherein the non-compliant balloon is polyethylene terepthalate.

12. A catheter as in claim 1 wherein the insulation region is located along the entire portion of the catheter shaft that is proximal to the heat exchange region.

13. A catheter as in claim 1 wherein the insulation region is located along less than the entire portion of the catheter shaft that is proximal to the heat exchange region.

14. A catheter as in claim 1 wherein the insulation region comprises an inflatable insulator having a radially collapsed configuration and a radially expanded configuration disposed on the catheter, and further comprising centering members positioned between the catheter shaft and the inflatable insulator to maintain the catheter shaft in a substantially centered position within the insulator when the insulator is in its inflated radially expanded configuration.

15. A catheter as in claim 14 wherein the centering members comprises tethers positioned between the exterior of the catheter shaft and the interior of the inflatable insulator.

16. A catheter as in claim 14 wherein the centering members comprises collapsible stand-offs on the exterior of the shaft.

17. A catheter as in claim 1 wherein at least one heat exchange fin is formed on the heat exchange region to increase the efficiency of heat exchange with body fluid or tissue.

18. A catheter as in claim 17 wherein the heat exchange fin comprises at least one lobe of a multi-lobed balloon.

19. An improved heat exchange catheter having an expandable insulation region, said catheter comprising:
   A a shaft having an inflow beat exchange channel and an outflow beat exchange channel
   B an inflow manifold and outflow manifold, said inflow manifold in fluid communication with said inflow heat exchange channel, said outflow manifold in fluid communication with said outflow heat exchange channel;
   C a heat exchange region, said heat exchange region comprising an inflatable balloon, said inflatable balloon having an interior volume and an exterior surface, and further said interior volume having an inflow end and an outflow end, said inflow end being in fluid communication with said inflow manifold, and said outflow end being in fluid communication with said outflow heat exchange channel; and
   D an elongate inflatable insulation sheath, said inflatable insulation sheath surrounding at least a substantial portion of said shaft, the insulation sheath being radially expandable from a first diameter to a second diameter that is larger than the first diameter.

20. A heat exchange catheter as in claim 19 wherein said balloon comprises a plurality of longitudinally extending tubes defining flow lumens, and further including a fluid flow path in the shaft for the flow of heat exchange fluid, the heat exchange region further including a manifold for delivering heat exchange fluid from the fluid flow path to a distal end of each of the flow lumens.

21. A heat exchange catheter as in claim 20 wherein at least some of the longitudinally extending tubes extend in a helical configuration.

22. A heat exchange catheter as in claim 19 wherein said heat exchange region is further constructed to perform a procedure selected from the group consisting of ablation, angioplasty, thermodilution, whole body temperature regulation, and regional temperature regulation.

23. A heat exchange catheter as in claim 19 wherein the heat exchange catheter is sized for insertion into the body through an insertion channel, said insertion channel being selected from the group consisting of a trocar, an insertion sheath, a percutaneous incision and a percutaneous puncture.

24. A heat exchange catheter as in claim 23 wherein the channel is 13 French or less in size.

25. A heat exchange catheter as in claim 19 wherein the shaft is configured for insertion into a blood vessel of a patient, and further including a source of inflation medium, wherein said source is regulated to generate an inflation pressure within the inflatable insulation sheath of no more than 2 psi above blood pressure in the vessel in which the sheath is located.

26. A heat exchange catheter as in claim 19 further including a source of inflation medium and a flow restrictor that limits inflow of inflation medium to the interior of the inflatable insulation sheath to a rate similar to the rate the inflation medium would be absorbed by the body.

27. A heat exchange catheter as in claim 26 wherein the flow restrictor limits inflow of inflation medium to the interior of the inflatable insulation sheath to a rate of between about 2–3 cc/min.

28. A heat exchange catheter as in claim 19 wherein the insulation sheath is located along the entire portion of the catheter shaft that is proximal to the heat exchange region.

29. A heat exchange catheter as in claim 19 wherein insulation sheath is located along less than the entire portion of the catheter shaft that is proximal to the heat exchange region.

30. A method of performing heat exchange at a target location, comprising:

(A) providing an elongate shaft having a proximal end and a distal end, the shaft having a heat exchange region and an elongate insulating region disposed thereon, the insulating region surrounding a substantial portion of the shaft proximal to the heat exchange region;

(B) inserting the catheter into the body through a channel having a diameter approximately equal to the diameter of the shaft, the insulating region having a first size about the shaft permitting its insertion through the channel;

(C) locating the heat exchange region into proximity with the target location;

(D) radially expanding the insulating region to a second size about the shaft larger than the first size to provide a thermal barier between the shaft and the body; and (E) exchanging heat between the heat exchange region and a body fluid or tissue at the target location in conjuction with heat flow along the shaft.

31. A method as in claim 30 wherein said channel is selected from the group consisting of:

trocars, insertion sheaths, percutaneous incisions and percutaneous punctures.

* * * * *